(12) United States Patent
Stapley et al.

(10) Patent No.: US 9,133,554 B2
(45) Date of Patent: *Sep. 15, 2015

(54) METHODS FOR THE ELECTROLYTIC PRODUCTION OF ERYTHRITOL

(75) Inventors: Jonathan A. Stapley, Bellevue, WA (US); J. David Genders, Elma, NY (US); Daniel M. Atherton, Lancaster, NY (US); Peter M. Kendall, East Amherst, NY (US)

(73) Assignee: Dynamic Food Ingredients Corporation, Kirkland, WA (US)

(*) Notice: Subject to any disclaimer, the term of this patent is extended or adjusted under 35 U.S.C. 154(b) by 1050 days.

This patent is subject to a terminal disclaimer.

(21) Appl. No.: 13/152,849

(22) Filed: Jun. 3, 2011

(65) Prior Publication Data
US 2011/0272291 A1    Nov. 10, 2011

Related U.S. Application Data

(63) Continuation-in-part of application No. 11/482,214, filed on Jul. 7, 2006, now Pat. No. 7,955,489.

(60) Provisional application No. 60/771,549, filed on Feb. 8, 2006.

(51) Int. Cl.
*C25B 3/00* (2006.01)
*C25B 3/04* (2006.01)
(Continued)

(52) U.S. Cl.
CPC .. *C25B 3/02* (2013.01); *C07H 1/00* (2013.01); *C07H 3/02* (2013.01)

(58) Field of Classification Search
CPC .............. C25B 3/00; C25B 3/02; C25B 3/04; C07C 27/00; C07C 27/04; C07C 27/26; C07C 29/74

USPC ............... 568/700, 840, 852, 861, 864, 872; 205/421, 443, 454
See application file for complete search history.

(56) References Cited

U.S. PATENT DOCUMENTS

| 3,632,802 A | 1/1972 | BeMiller et al. ........ 260/233.3 R |
| 4,457,813 A | 7/1984 | Rogers et al. ................... 204/74 |

(Continued)

FOREIGN PATENT DOCUMENTS

| EP | O 999 197 A2 | 5/2000 |
| JP | 07-504667 | 5/1995 |

(Continued)

OTHER PUBLICATIONS

Andrews et al., "Decarbonylation of Unprotected Aldose Sugars by Chlorotris(triphenylphosphine)rhodium(I). A New Descent of Series Approach to Alditols, Deoxyalditols, and Glycosylalditols," *J. Org. Chem.*, 1989, 54. 5257-5264.

(Continued)

*Primary Examiner* — Edna Wong
(74) *Attorney, Agent, or Firm* — Brinks Gilson & Lione; Ryan L. Marshall (57) ABSTRACT

Methods for the production of erythrose and/or erythritol are provided herein. Preferably, the method of producing erythritol includes the step of electrolytic decarboxylation of a ribonic acid or arabinonic acid reactant to produce erythrose and the step of electrolytic reduction or erythrose to produce erythritol. Optionally, the reactant can be obtained from a suitable hexose sugar, such as allose, altrose, glucose, fructose or mannose.

18 Claims, 4 Drawing Sheets

(51) Int. Cl.
C25B 3/02 (2006.01)
C07H 1/00 (2006.01)
C07H 3/02 (2006.01)

(56) References Cited

U.S. PATENT DOCUMENTS

| | | | | |
|---|---|---|---|---|
| 4,950,366 | A * | 8/1990 | Jiricny et al. | 205/348 |
| 5,563,303 | A | 10/1996 | Vuorinen | 568/864 |
| 5,599,435 | A | 2/1997 | Li et al. | 205/59 |
| 5,998,608 | A | 12/1999 | Tamion | 536/124 |
| 6,262,318 | B1 | 7/2001 | Heikkilä et al. | 568/864 |
| 6,300,494 | B1 | 10/2001 | Fleche et al. | 536/124 |
| 7,955,489 | B2 * | 6/2011 | Stapley et al. | 205/421 |
| 2005/0272961 | A1 | 12/2005 | BeMiller et al. | 568/863 |

FOREIGN PATENT DOCUMENTS

| | | | |
|---|---|---|---|
| JP | 2001-203007 | 7/2001 | |
| WO | WO 2005/095314 | 10/2005 | |
| WO | WO 2005/095314 A1 | 10/2005 | |
| WO | WO 2005095314 A1 * | 10/2005 | C07C 31/18 |

OTHER PUBLICATIONS

Andrews et al., "Decarbonylation of Sugars by Chlorotris(triphenylphosphine)rhodium," *J Chem. Soc., Chem. Commun.*, 1988 1266-1267.
Antonovskii et al., "Use of dulcitol obtained during the hydrogenation of water-soluble larch substances," *Wood Products*, vol. 76, 1972 (155857c).
Baggett et al., "Aspects of Stereochemistry. Part XXIV. The Acid-catalysed Rearrangement of 2,4-O-Benzylidene-D-erythrose and 2,3-O-Benzylidene-erythritol," *J. Chem. Soc. (C)*, 1966 212-215.
Barker et al., "Some Oxidation and Reduction Products of 2,4-O-Ethylidene-D-erythrose," *J. Am. Chem. Soc.*, 1960, 82:2301-2303.
Barker et al., "Aspects of Stereochemistry. Part XIII. Properties of Some Disubstituted Derivatives of 5-Hydroxy-1,3-dioxan," *J. Chem. Soc.*, 1963, 4161-4167.
Besson et al., "Catalytic Oxidation of Glucose on Bismuth-Promoted Palladium Catalysts", J. of Catalysis (no month, 1995), vol. 152, pp. 116-121.
Blanc et al., "Starch-derived polyols for polymer technologies: preparation by hydrogenolysis on metal catalysts," *Green Chemistry*, Apr. 2000 89-91.
Elseviers et al., "Downstream Processing of Oxidative Decarboxylated Carbohydrates. Comparison Between Ion Exchange Resins and Electrodialysis", PharmaChem (no month, 2003), vol. 2, Nos. 7-8, pp. 47-53. Abstract Only.
Elseviers et al., "Method for the production of meso-erythritol by the hydrogenation and isomerization of tartaric acid," *Chemical Abstracts*, 33-Carbohydrates, vol. 126, No. 20, 1997, (264309x).
Hay et al., "Electrolysis of low molecular weight carbohydrates in non-aqueous media. I. The products of electrolysis of monosaccharides," Canadian Journal of Chemistry, vol. 47, pp. 417-421, 1969, XPOO9089500.
Kent et al., "Fluorocarbohydrates. Part VIII. Formation of Halogenoderivatives from Aliphatic Diazo-compounds," *J. Chem. Soc.*, 1964, 2493-2497.
Lespieau, R., "Synthesis of Erythrite," *Organic Chemistry*, 1907, 982-983.
Lespieau, R., "Synthesis of y-Erythronic Acid and i-Erythrite," *Bull. soc. chem.*, (4) 1908, 1112-20.
Murata et al., "Preparation of polyols by catalytic reductive condensation of formaldehyde," *Chemical Abstracts*, vol. 110, 1989.
Otey et al., "Erythritol and Ethylene Glycol from Dialdehyde Starch," *Industrial and Engineering Chemistry*, vol. 53, No. 4, Apr. 1961 267-268.
Otey et al., "Erythritol and ethylene glycol," *Chemical Abstracts*, 58, 1963.
Pariselle et al., "New Synthesis of Natural and of Racemic Erythrite," *Chemical Abstracts*, 4, 1910, 2100.
Pariselle et al., "Glycerol with Four Carbon Atoms. Passage to the Furfurane Series and to the Erythritols," *Chemical Abstracts, 6, 1912*, 608-610.
Poletaeva et al., "Study of glucose hydrogenolysis on nickel-alumina and nickel-copper-alumina catalysts," *Chemical Abstracts*, Vo. 86, 1977 (90160e).
Raphael et al., "Synthesis of Carbohydrates by Use of Acetylenic Precursors. Part II. Addition Reactions of cis-and trans-*But-2-ene*-1: 4-*diol* Di-acetates. Synthesis of DL-Erythrulose,"*J Chem. Soc.*, 1952, 401-405.
Stefoglo et al., "Kinetic model for the preparation of glycerol by the catalytic hydrogenolysis of glucose," *Wood Products*, vol. 80, 1974, 87-89.
Vallieres et al., "A Multisectioned Porous Electrode for Synthesis of D-Arabinose", J. of the Electrochem. Soc. (no month, 1999), vol. 146, No. 8, pp. 2933-2939.
Vasyunina et al., "Preparation of glycerol and glycols," *Chemical Abstracts*, vol. 62, 1965.
Vasyunina et al., "Preparation of glycerol and glycols by hydrogenolysis of xylitol," *Khim. Prom.*, 1962, 82-86.
Vasyunina et al., "Hydrogenation of xylitol. II. Effect of promoters," *Chem. Abstr.*, vol. 59, 1963.
Vasyunina et al., "Xylitol hydrogenolysis. I. Effects of temperature and pressure," *Chemical Abstracts*, vol. 59, 1963.
Hay G.W., Smith F., "Electrolysis of low molecular weight carbohydrates in non-aqueous media. I. The products of electrolysis of monosaccharides," *Canadian Journal of Chemistry*, 47:417-421 (1969).
Office Action for Japanese Application No. 2008-554231, dated Oct. 4, 2011 (5 pages).

* cited by examiner

METHODS FOR THE ELECTROLYTIC PRODUCTION OF ERYTHRITOL

RELATED APPLICATIONS

The present patent document is a continuation-in-part of application Ser. No. 11/482,214, filed Jul. 7, 2006, now U.S. Pat. No. 7,955,489, issued Jun. 7, 2011, which claims the benefit of the filing date under 35 U.S.C. §119(e) of Provisional U.S. Patent Application No. 60/771,549, filed Feb. 8, 2006. All of the foregoing applications are hereby incorporated by reference.

TECHNICAL FIELD

The present disclosure relates to methods of producing erythrose and/or erythritol.

BACKGROUND

Erythritol, a naturally occurring polyol sweetener, can be used to replace sugar while preserving the sweet taste. Erythritol is a four-carbon sugar polyol (tetritol), which possesses several properties such as sweetness (about 60-80% of sucrose), tooth friendliness, very low calorific value (0.2 kcal/g, 5% that of sucrose), non-carcinogenicity and, unlike other polyols, causes little, if any, gastro-intestinal discomfort (Harald and Bruxelles (1993) Starch/Starke 45:400-405). Further, erythritol possesses desirable processing properties such as heat-stability, and minimal undesirable reactivity with amino groups so as to resist browning of when present in an organic substance. Erythritol can be used as a sweetener, for example in beverages. For example, U.S. Pat. Nos. 4,902,525 and 6,066,345, JPA 7-274829 and EP 0 759 273 relate to the addition of erythritol to beverages for purposes of flavor enhancement. A chewing gum made with a sweetening agent containing erythritol and a liquid sugar or sugar alcohol is disclosed in U.S. Pat. No. 5,120,550. A method of reducing dental cavities by administering a sugarless chewing gum made with erythritol is disclosed in European Patent Publication No. 0 009 325. Low-caloric sweetening compositions containing mesoerythritol are disclosed in U.S. Pat. No. 5,080,916 and No. 4,902,525 and Japanese Patent Publications No. 89-225458 and 90-104259. Japanese Patent Publication No. 89-51045 discloses chewing gum made with a melted mixture of mesoerythritol and sugars or sugar alcohols. A sweetener employing the use of spray dried erythritol is disclosed in European Patent Publication No. 0 497 439. A sweetening composition made up of erythritol, sorbitol and a glucose oligomer is disclosed in European Patent Publication No. 0 511 761.

Erythritol can be found in lichens, hemp leaves, and mushrooms. Erythritol may also be found in fermented foods such as wine, soya sauce, or saki (Sasaki, T. (1989) Production technology of erythritol. Nippon Nogeikagaku Kaishi 63: 1130-1132). Industrial erythritol production is typically carried out by one of two approaches: chemical synthesis or fermentative biosynthesis.

Chemical synthesis of erythritol typically includes the addition of catalysts such as hydrogen and nickel to the raw material sugars under the environment of high temperature and high pressure. Decarboxylation reactions can be performed with hydrogen peroxide or hypochlorite, for instance. A suitable method is the so-called Ruff reaction, utilizing a combination of hydrogen peroxide and ferrous sulphate as a catalytic agent (see e.g. Ruff, *Berichte der Deutschen Chemischen Gesellschaft* 32 (1899) 553-554, and E. Fischer, O. Ruff, Ber. 33 (1900) 2142). Reduction can be carried out chemically, for instance by catalytic hydrogenation, or enzymatically. For example, calcium D-arabinonate may be in the presence of aqueous hydrogen peroxide solution. Other processes for the manufacture of D-erythrose include the oxidation of D-glucose in the presence of lead tetraacetate, known under the name of the Perlin method (Perlin A. S., Methods Carbohydr. Chem., 1962, 1, 64), or the acid hydrolysis of 2,4-O-ethylidene-D-erythrose obtained by the oxidation with periodate of 4,6-O-ethylidene-D-glucose (Schaffer R., J. Am. Chem. Soc., 81 (1959), 2838; Barker R. and MacDonald D. L., J. A. Chem. Soc., 82 (1960), 2301). A few improvements in the conversion of gluconic acid to D-arabinose have subsequently been introduced by R. C. Hockett and C. S. Hudson (J. Amer. Chem. Soc., 56, 1632-1633, (1934) and ibid., 72, 4546, (1950)) and by the document U.S. Pat. No. 3,755,294. Arabinose yields of 60%, starting from gluconic acid, are described therein. Progress has been accomplished by V. Bilik (CZ-232647, (1983)) by using cupric (Cu(II)) ions as catalysts. Yields of the order of 70% are achieved after a laborious purification. Identical results were recently obtained with a mixture of ferric and ferrous ions as catalysts (CZ-279002, (1994)). Finally, under specific conditions, the document EP-A 0,716,067 reports yields of certain aldoses of 78%. Another process is performed by the chemo-reduction of raw materials such as meso-tartarate (Kent, P. W., and Wood, K. R. (1964) J. Chem. Soc. 2493-2497) or erythrose (Otey, F. H., and Sloan, J. W. (1961) Ind. Eng. Chem. 53:267) to obtain erythritol. None of the known chemical synthesis techniques, such as reduction of meso-tartrate, oxidation/reduction of 4,6-O-ethylidene-D-glucose and hydrogenation of starch dialdehyde hydrolysates (T. Dola and T. Sasaki, Bio-Industry, (1988), 5, (9), 32), has been widely used for widespread industrial production. Still other chemical processes developed for the production of erythritol include the hydrogenation of tartaric acid to yield mixtures of tetritols, including erythritol (U.S. Pat. No. 5,756,865). Tartaric acid esters have also been reduced to yield erythritol (U.S. Pat. No. 2,571,967).

In addition, erythritol can be produced by a number of microorganisms. For example, the erythritol can be produced by fermenting glucose with specialized yeast strains has been described U.S. Pat. No. 5,902,739. Recovery of erythritol from fermentation broths is described in U.S. Pat. No. 6,030,820, U.S. Pat. No. 6,440,712 and U.S. Pat. No. 4,906,569. Microorganisms useful in the production of erythritol include high osmophilic yeasts, e.g., *Pichia, Candida, Torulopsis, Trigonopsis, Moniliella, Aureobasidium*, and *Trichosporon* sp. (Onishi, H. (1967) Hakko Kyokaish 25:495-506; Hajny et al. (1964) Appl. Microbiol. 12:240-246; Hattor, K., and Suziki, T. (1974) Agric. Biol. Chem. 38:1203-1208; Ishizuka, H., et al. (1989) J. Ferment. Bioeng. 68:310-314.) Production of erythritol by various yeasts have been reported: *Debaryomyces* (U.S. Pat. No. 2,986,495), *Pichia* (U.S. Pat. No. 2,986,495), *Candida* (U.S. Pat. No. 3,756,917), *Moniliella* (Antonie van Leeuwenhoek, 37 (1971), 107-118), and *Aureobasidium* (JP-A 61/31,091). Two microorganisms, namely, *Moniliella tomentosa* var. *pollinis* CBS461.67 and *Aureobasidium* sp. SN-G42 FERM P-8940, are known currently to be employed practically to produce erythritol. The former is employed, for example, in methods for producing polyols in an industrial scale by means of fermentation of saccharides (Japanese Patent Publication No. 6-30591 (30591/1994), ibid. 6-30592 (30592/1994), ibid. 6-30593 (30593/1994), ibid. 6-30594 (30594/1994)), and in these publications methods for producing a series of polyols including erythritol are disclosed. However, the strain of *Moniliella tomentosa* var. *pollinis* employed in such methods has a poor saccharide resistance and suffers from reduced yield of erythritol at a high saccharide concentration. Thus, at the saccharide concentration of 25 w/v % the saccharide-based erythritol yield (amount of erythritol produced relative to the amount of saccharide consumed) is as high as 42%, but at the saccharide concentration as high as 35 w/v % the saccharide-based erythritol yield is 33%, and at 35 w/v % the yield is as markedly low as 27%. Often, studies carried out on fermentation techniques produce erythritol as a secondary constituent. Possible disadvantages in the production of erythritol by fermentation include foaming during fermentation, an undesirably slow rate of fermentation, the amount of the byproducts and poor yield.

One of the major drawbacks of the use of erythritol as a sugar replacer is that it is much more expensive than some of the substances which it replaces. There is a need for improved, cost-effective processes for the manufacture of erythritol, or D-erythrose (converted to erythritol by hydrogenation of the D-erythrose thus obtained).

SUMMARY

The present disclosure relates to new cost-effective methods of producing erythrose or erythritol. In one particular embodiment, the disclosure provides a method of producing erythritol comprising the steps of providing a solution comprising arabinonic acid or ribonic acid; electrolytically oxidatively decarboxylating the arabinonic acid or ribonic acid at an anode to produce erythrose; and electrolytically reducing the erythrose at a cathode to produce erythritol. Preferably the decarboxylating and reducing are done concurrently as part of the same circuit. The reducing of erythrose may be accomplished by contacting the erythrose with a cathode comprising Pb, Cu, Cd, Hg, Zn, Ni, Ru, Rh, Pt, Fe, steels, amalgams thereof or alloys thereof, preferably Pb, Cu, Zn, Ni, or Pt, more preferably Nickel foam, Raney Nickel, or Nickel Aluminum alloy, even more preferably Raney Nickel. In some aspects the cathode comprises a catalytic amount of Ru on a conducting substrate. The oxidative decarboxylating of ribonic acid or arabinonic acid may be accomplished by contacting the ribonic acid or arabinonic acid with an anode comprising graphite, pyrolytic carbon, wax-impregnated graphite, glassy carbon, dispersed graphite, dispersed carbonaceous material, carbon cloth, coke, or platinum as a planer, packed bed, fluidized bed, or porous anode, preferably a graphite foil electrode. At least 10% of the ribonic acid or arabinonic acid may be neutralized or exist as the corresponding salt thereof, preferably about 10%-100%; more preferably about 35%-80%, even more preferably about 40%-60%, and yet more preferably about 50%. The degree of neutralization may be maintained by electrodialysis. The electrolytic cell may be a divided, undivided, flow-through or batch electrolytic cell, and may be configured as a monopolar or bipolar electrolytic cell. In some aspects, the method may further comprise the step of decarboxylating a sugar to produce ribonic acid or arabinonic acid, the sugar selected from the group consisting of allose, altrose, glucose, fructose and mannose. In some aspects, the method may comprise the steps of providing an aqueous solution comprising a salt selected from the group consisting of arabinonate and ribonate; and acidifying the aqueous solution to provide the solution having between about 35% and about 80% of the arabinonic acid or ribonic acid neutralized. The acidifying may comprise adding ribonic acid or arabinonic acid to the aqueous solution, contacting the aqueous solution with an ion exchange resin, using electrodialysis or contacting the aqueous solution with a divided electrolytic cell with a cation exchange membrane. In some aspects, arabinonic acid or ribonic acid may be removed from the crude erythritol product formed by electrodialysis or by contacting the crude solution product with an ion exchange resin.

In a first embodiment, the methods include the step of electrolytic decarboxylation of an arabinonic or ribonic acid, to produce erythrose. The electrolytic decarboxylation step can be performed using a highly crystalline carbon anode. The arabinonic or ribonic acid reactant is preferably maintained in a solvent, with about 35-80% of the arabinonic or ribonic acid neutralized, more preferably about 50% neutralized, prior to or during the electrolytic decarboxylation step. The solvent is preferably water, although other solvents can also be used. For example, the acid solution can be an aqueous solution comprising 50% arabinonic acid and 50% arabinonate salt or 50% ribonic acid and 50% ribonate salt, and the temperature can be maintained at about 25° C., when the electrolytic decarboxylation step is started. Preferably, the electrolytic decarboxylation step is stopped at about 80% conversion of the acid followed by recycling of the residual acid. Alternatively, the pH may be controlled by ion exchange or adding un-neutralized starting acid during the electrolytic decarboxylation.

Any suitable arabinonic or ribonic acid capable of producing erythrose as a product of the electrolytic decarboxylation step can be used. In a first aspect, the reactant can be a ribonic acid, arabinonic acid, or a mixture thereof, including meso-, d- or l-stereoisomers thereof. In a second aspect, the erythrose product can be meso-erythrose, D-erythrose or L-erythrose, or purified stereoisomers thereof. Preferably, the reactant of electrolytic decarboxylation step is meso-, d- or l-arabinonic acid, and the product is the resulting form of meso-, d- or l-erythrose.

In a second embodiment, the arabinonic or ribonic acid reactant is obtained from a suitable hexose sugar starting material by any suitable method. Preferably, the starting material is selected from the group consisting of allose, altrose, glucose, fructose and mannose, including any meso-, d- or l-forms thereof. More preferably, the starting material is d-glucose, fructose or d-mannose. The starting material can be converted to an arabinonic or ribonic acid by one or more reaction steps. Preferably, a suitable C-6 sugar starting material is decarboxylated at the C-1 position by a suitable reaction. For example, D-arabinonic acid may be prepared by oxidizing D-glucose with oxygen gas in an alkaline water solution, oxidation of D-fructose, oxidizing D-glucose with pyranose-2-oxidase to D-arabino-hexos-2-ulose followed by treatment with a hydroperoxide, or the oxidation of D-glucose to D-arabino-2-hexylosonic acid (or its salt) followed by decarboxylation with hydrogen peroxide or its salt. Optionally, the hexose sugar starting material can be synthesized or obtained from any suitable source or by any suitable synthesis or purification method(s).

In a third embodiment, an erythrose product of the electrolytic decarboxylation step can be subsequently hydrogenated by any suitable method to provide erythritol. For example, erythrose can be reduced by using hydrogen and a hydrogenation catalyst to produce erythritol. The reduction can be performed using any suitable reaction, such as a ruthenium or nickel catalyst. In one aspect, a hydrogenation can be performed at temperatures between 70° C. and 150° C., and at pressures between 0.1 and 10 MPa $H_2$. Alternatively, electrochemical reduction may be used.

In one particular embodiment, the disclosure provides a method of producing erythrose comprising the step of electrolytically decarboxylating an acid selected from the group consisting of a ribonic acid and an arabinonic acid in solution to produce erythrose. The method may optionally further comprise the step of reducing the erythrose at a cathode to produce erythritol. The acid is preferably provided as an aqueous aldonic acid solution comprising the ribonic acid and/or the arabinonic acid. Preferably, the acid is a 5-carbon carboxylic acid placed in contact with a highly graphitic anode to permit electrolytic decarboxylation of the acid to produce erythrose. The ribonic acid and/or the arabinonic acid in the acid solution is preferably provided in a separate step by decarboxylating a sugar selected from the group consisting of: allose, altrose, glucose, fructose and man nose, or derivatives, analogs or salts thereof to produce the acid. Optionally, ribonic acid may be provided by the epimerization of arabonic acid. For example, U.S. Pat. No. 4,778,531 to Dobler et al., filed Jun. 30, 1987 and incorporated herein by reference, describes methods for the epimerization of D-arabinose to D-ribose. The acid solution is preferably provided by combining an aldonic acid, such as ribonic or arabinonic acid, with a solvent such as water or a water-miscible solvent to produce the acid solution. For example, one particularly preferred method of producing erythritol comprises the steps of: (a) oxidatively decarboxylating a sugar selected from the group consisting of: allose, altrose, glucose, fructose and man nose, to provide an acid comprising a 5-carbon carboxylic acid, preferably an aldonic acid; (b) combining the carboxylic acid with a solvent to produce an aldonic acid solution; (c) electrolytically decarboxylating the 5-carbon carboxylic acid in the aldonic acid solution to produce erythrose; and (d) reducing the erythrose at a cathode to produce erythritol. Preferably, the aldonic acid solution has between about 10% and 100%, more preferably about 35% to 85%, most preferably about 50%, of the acid neutralized prior to the electrolytic decarboxylation. Residual aldonic acid from the decarboxylation step may be recycled by contacting unreacted aldonic acid with an ion exchange material or adding non-neutralized acid, followed by repeating the oxidative decarboxylation step to produce erythrose.

DETAILED DESCRIPTION

The methods for the production of erythrose and/or erythritol disclosed in the present disclosure preferably include the step of the decarboxylation of an arabinonic or ribonic acid substrate. The decarboxylation step can be an oxidative decarboxylation performed by an electrolytic decarboxylation of an arabinonic or ribonic acid reactant to produce an erythrose product. Preferably, the erythrose is reduced at a cathode to produce erythritol.

Definitions

As used herein, the term "aldonic acid" refers to any polyhydroxy acid compound comprising the general formula $HOCH_2[CH(OH)]_nC(=O)OH$ (where n is any integer, including 1-20, but preferably 1-12, more preferably 5-8), as well as derivatives, analogs and salts thereof. Aldonic acids can be derived, for example, from an aldose by oxidation of the aldehyde function (e.g., D-gluconic acid).

Recitation of "erythrose" herein refers to an aldose (tetrose) carbohydrate with chemical formula $C_4H_8O_4$, including any stereoisomers, derivatives, analogs and salts thereof. Unless otherwise indicated, recitation of "erythrose" herein is intended to include, without limitation, the molecules: D-(−)-Erythrose, L-(+)-Erythrose, D(−)-Erythrose, D-Erythrose, L-Erythrose and D(−)-Erythrose and meso-erythrose. A Fischer Projection of the D-erythrose structure (1) is provided below.

(1)

The term "erythritol" herein, unless otherwise specified, includes molecules with the chemical formula $C_4H_{10}O_4$, as well as any stereoisomers, derivatives and analogs thereof. Unless otherwise indicated, recitation of "erythrose" herein is intended to include, without limitation, the molecules: D-(−)-meso-erythritol, (D)-Erythritol, (L)-Erythritol, (R*,S*)-1,2,3,4-butanetetrol; (R*,S*)-tetrahydroxybutane; erythrol; erythrite; 1,2,3,4-butanetetrol, (R*,S*)-; erythritol, and phycitol. A Fischer Projection of the D-erythritol structure (2) is provided below.

(2)

The term "decarboxylation" as used herein refers to the removal of a carboxyl group (—COOH) by a chemical reaction or physical process. Typical products of a decarboxylation reaction may include carbon dioxide ($CO_2$) or formic acid.

The term "electrochemical" refers to chemical reactions that can take place at the interface of an electrical conductor (an electrode) and an ionic conductor (the electrolyte). Electrochemical reactions can create a voltage potential between two conducting materials (or two portions of a single conducting material), or can be caused by application of external voltage. In general, electrochemistry deals with situations where an oxidation and a reduction reaction is separated in space. The term "electrolytic" as used herein refers to an electrochemical oxidation or reduction reaction that results in the breaking of one or more chemical bonds. Electrolytic reactions as used herein preferably describe reactions occurring as a product of interaction with a cathode or anode.

As used herein, "derivative" refers to a chemically or biologically modified version of a chemical compound that is structurally similar to a parent compound and (actually or theoretically) derivable from that parent compound. A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group) that do not substantially alter the function of the molecule for a desired purpose. The term "derivative" is also used to describe all solvates, for example hydrates or adducts (e.g., adducts with alcohols), active metabolites, and salts of the parent compound. The type of salt that may be prepared depends on the nature of the moieties within the compound. For example, acidic groups, for example carboxylic acid groups, can form, for example, alkali metal salts or alkaline earth metal salts (e.g., sodium salts, potassium salts, magnesium salts and calcium salts, and also salts quaternary ammonium ions and acid addition salts with ammonia and physiologically tolerable organic amines such as, for example, triethylamine, ethanolamine or tris-(2-hydroxyethyl)amine). Basic groups can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds which simultaneously contain a basic group and an acidic group, for example a carboxyl group in addition to basic nitrogen atoms, can be present as zwitterions. Salts can be obtained by customary methods known to those skilled in the art, for example by combining a compound with an inorganic or organic acid or base in a solvent or diluent, or from other salts by cation exchange or anion exchange.

As used herein, "analogue" refers to a chemical compound that is structurally similar to another but differs slightly in composition (as in the replacement of one atom by an atom of a different element or in the presence of a particular functional group), but may or may not be derivable from the parent compound. A "derivative" differs from an "analogue" in that a parent compound may be the starting material to generate a "derivative," whereas the parent compound may not necessarily be used as the starting material to generate an "analogue."

Any concentration ranges, percentage range, or ratio range recited herein are to be understood to include concentrations, percentages or ratios of any integer within that range and fractions thereof, such as one tenth and one hundredth of an integer, unless otherwise indicated. Also, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to one polymer or a mixture comprising two or more polymers. As used herein, the term "about" refers to differences that are insubstantial for the relevant purpose or function.

Electrochemical Decarboxylation

Figure 1A:
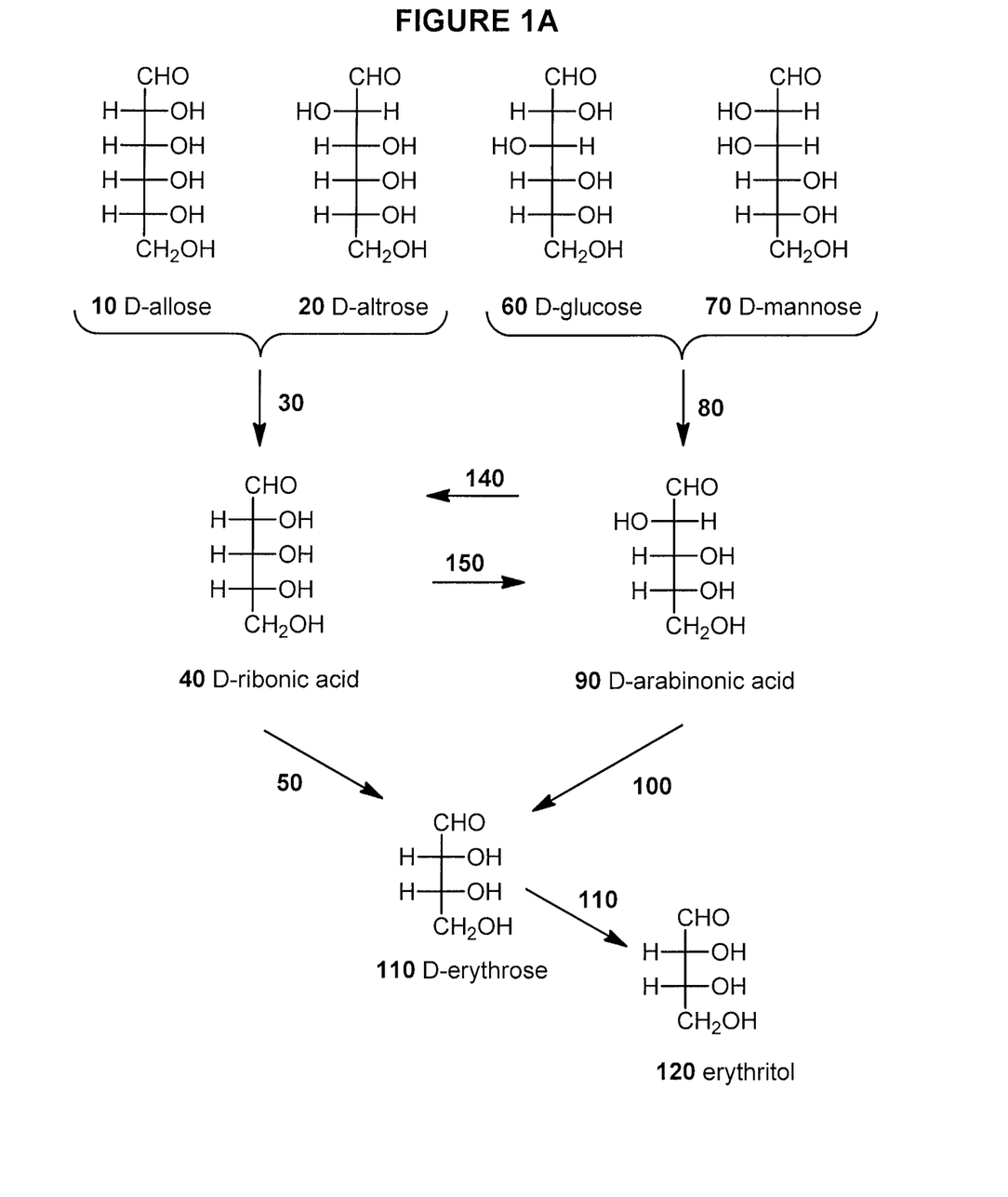
FIG. 1A is a reaction scheme showing various reaction steps using certain allose, altrose, glucose or mannose starting materials.

The step of electrochemical oxidative decarboxylation of a reactant substrate is preferably performed on the reactant substrate. FIG. 1A shows a schematic diagram describing various methods related to the production of erythrose and erythritol. Preferably, the methods include the step of electrolytic decarboxylation of a suitable reactant to produce erythrose. The reactant can be provided as a solution of the reactant placed in contact with an electrode to effect a decarboxylation of the reactant so as to produce an erythrose.

According to a first embodiment, any suitable arabinonic or ribonic acid capable of producing erythrose as a product of an electrolytic decarboxylation step can be used as a reactant. The reactant is preferably a 5-carbon carboxylic acid, such as a ribonic acid or an arabinonic acid, including one or more stereoisomers (e.g., D-, L-, or meso-forms) or enantiomers of the reactant products, as well as suitable derivatives, analogs and salts of the reactants. Suitable reactants include derivatives and analogs of the carboxylic acid reactant can include reactants with chemical structure variations that insubstantially vary the reactivity of the molecule from undergoing an electrolytic decarboxylation process to produce either erythrose or an intermediate that can be converted to erythrose. For example, reference to an "arabinonic acid" reactant includes D-arabinonic acid, L-arabinonic acid and meso-arabinonic acid. In certain preferred aspects of the first embodiment, the reactant can be a ribonic acid, arabinonic acid, or a mixture thereof, including meso-, d- or l-stereoisomers thereof; the erythrose product can be meso-erythrose, D-erythrose or L-erythrose, or purified stereoisomers thereof. Preferably, the reactant of electrolytic decarboxylation step is meso-, d- or l-arabinonic acid, and the product is the resulting form of meso-, d- or l-erythrose.

FIG. 1A shows a first aspect of the first embodiment, whereby a D-ribonic acid is a first reactant 40 that undergoes a decarboxylation reaction 50 to produce a D-erythrose product 110. Also shown is an alternative aspect of the first embodiment, wherein a D-arabinonic acid is a second reactant 90 that undergoes an oxidative decarboxylation reaction 100 to produce the D-erythrose product 110. Optionally, the first reactant 40 can be obtained by a first conversion reaction 140 of D-arabinonic acid to D-ribonic acid. Alternatively, the second reactant 90 can be obtained by a second conversion reaction 150 of D-ribonic acid to D-arabinonic acid. While the decarboxylation reactions 50, 100 are preferably decarboxylation reactions that produce an aldehyde product, although other reaction products such as carboxylic acids can also be produced and preferably partially reduced to provide the aldehyde product 110, such as D-erythrose.

Preferably, the decarboxylation reaction 50, 100 is performed electrochemically. In one aspect, electrolytic decarboxylation of a reactant in a solution provides a desired product or intermediate that can be subsequently converted to the desired product. Preferably, the reactant is a ribonic acid, such as D-ribonic acid, or an arabinonic acid, such as D-arabinonic acid, and the product is an erythrose, such as D-erythrose. The reactant can be provided in a suitable solution comprising at least the reactant and a solvent. The reactant can be dissolved in the solvent by any suitable method, including stirring and/or heating where appropriate. The solvent can be any solvent in which the reactant can dissolve to a desired extent. Preferably, the solvent is water, any water-miscible solvent such as an alcohol, or a combination thereof. For example, solvents can comprise one or more of the following: water, methanol, ethanol, propanol, dioxane and acetonitrile. The solution is preferably an acidic solution comprising a ribonic acid or arabinonic acid, or a combination thereof.

Preferably, at least about 10% of the acid is neutralized or exists as a corresponding salt thereof. For example, the acid reactant solution can be provided with about 10, 20, 30, 40, 50, 60, 70, 80, 90, or 100% of one or more reactant acids neutralized. Preferably, 10%-100% of at least one ribonic acid or arabinonic acid reactant is neutralized. More preferably, about 35%-80% of a ribonic acid or arabinonic acid reactant present is neutralized, even more preferably about 40%-60%. Most preferably, about 50% of the ribonic acid or arabinonic acid reactant present in a reactant acid solution is neutralized.

In one aspect, the reactant acid solution is provided at about 10-100% neutralization, more preferably about 35-80% neutralization, even more preferably about 40-60% neutralization, and most preferably about 50% neutralization of the reactant acid. The pH can be permitted to increase as the electrolytic reaction proceeds. Optionally, the pH or percent neutralization could be provided and/or maintained within a desirable range throughout the reaction, for example by conducting the reaction in contact with an ion exchange resin or removing reactant acid solution after partial electrolysis and contacting it with ion exchange resin. The pH or percent neutralization could also be controlled by the addition of non-neutralized starting acid. The pH or percent neutralization could also be controlled by using a divided electrolytic cell with a cation exchange membrane. Alternatively, the pH or percent neutralization could be controlled by removing reactant acid solution after partial electrolysis and subjecting it to electrodialysis. The reactant acid solution can have any suitable pH to provide a desired concentration of dissociated reactant. For a reactant acid solution comprising an ribonic acid, the pH is preferably between about 3.0 and 6.0 prior to beginning the decarboxylation reaction. For a reactant solution comprising an arabinonic acid reactant, the pH is preferably between 3.0 and 6.0 prior to beginning the decarboxylation reaction.

Optionally, the residual reactant can be recycled by separating the starting material from products, for example by use of an anionic exchange resin. A partially decarboxylated solution of acid can contain both the starting acid (e.g., arabinonic acid) and the product (e.g., erythrose and erythritol). The negatively charged arabinonic acid can adhere to positively charged anionic exchange media. A partially reacted solution can be passed over a bed or column of ion exchange resin beads to replace the arabinonate with OH—. The solution can then be passed over cationic resin to strip any cations and neutralize the OH—. The resulting solution can comprise higher levels of the nonionic species (e.g., erythrose and erythritol). Once the anionic exchange resin is saturated with arabinonate, it can be removed by treating the resin with OH—. While the ion exchange resin recycling process has been illustrated with respect to hydroxyl (OH—) functional groups, other suitable groups may also be employed. Similarly, residual starting acid can be removed from reactant solution by electrodialysis. For example, residual arabinonic acid or ribonic acid may be removed by electrodialysis from the crude erythritol product formed from electrolytically reducing the erythrose. Residual arabinonic acid or ribonic acid may be removed by electrodialysis from the erythrose product formed from electrolytically oxidatively decarboxylating arabinonic acid or ribonic acid. Arabinonic acid or ribonic acid isolated by electrodialysis may be recycled in the oxidative decarboxylation.

Electrolytic Apparatus

The electrochemical decarboxylation of a suitable acid reactant can be performed using any suitable structure. Preferably, the electrochemical decarboxylation is performed by contacting an acid reactant solution comprising a ribonic acid or an arabinonic acid with an anode, where the reactant can be oxidized and decarboxylated. Contact between the starting material and the anode can elicit the decarboxylation, which can result in liberation of carbon dioxide and formation of a product such as erythrose. The product of the decarboxylation is preferably an aldehyde such as erythrose, or an intermediate such as an analog or derivative of erythrose that can be converted to erythrose or other suitable aldehyde.

Figure 3:
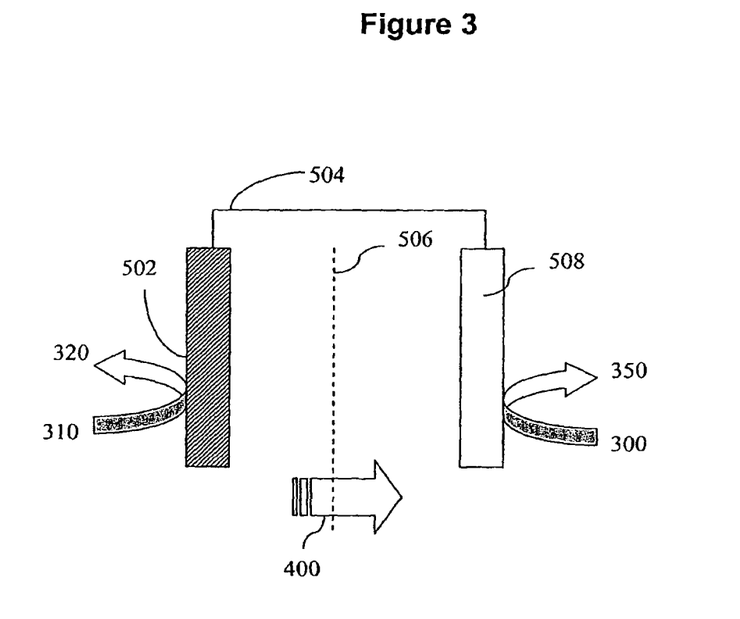
FIG. 3 is a schematic of an electrolytic oxidative decarboxylation step for the production of erythrose.

Preferably, the electrochemical decarboxylation of the reactant is conducted in an apparatus having any configuration comprising an anode in electrically conducting communication with a cathode. FIG. 3 shows a schematic of an electrochemical apparatus for decarboxylation of a reactant acid to form a desired product, such as erythrose. The apparatus comprises an anode 502 connected through a means for electrical conduction 504 to a cathode 508.

The anode 502 preferably comprises a carbon reactive surface where oxidation of the reactant acid can occur. The electrochemical cell anode can be formed from any suitable material such as graphite, pyrolytic carbon, wax-impregnated graphite, glassy carbon, dispersed graphite, dispersed carbonaceous material, carbon cloth, coke, or platinum as a planer, packed bed, fluidized bed, or porous anode. Most preferably, the anode reactant surface comprises a highly crystalline graphitic material, such as a graphite foil. Other, less preferred, materials such as platinum or gold can also be used to form the reactive surface of the anode. The reactant acid 310 can be a ribonic acid or arabinonic acid that is oxidized at or near the reactant surface of the anode 502 to form a product 320 such as erythrose. The anode surface area is preferably large and is preferably made of a carbonaceous material, platinum, or other metal.

Preferably, the electrochemical cell further comprises a cathode 508, where a reduction can occur within the electrochemical cell. The cathode 508 can be formed from any suitable material having a desired level of electrical conductivity, such as stainless steel. In one aspect, the decarboxylation reaction at the anode can be:

$$\text{arabinate} - 2e^- \rightarrow \text{erythrose} + CO_2 + 2H^+$$

The counter electrode reaction can be:

$$2H_2O + 2e^- \leq 2OH^- + H_2$$

Typically, some current can be lost to the production of $O_2$ gas at the anode.

In a preferred aspect, the reactant erythrose 300 is reduced at or near the reactant surface of the cathode 508 to erythritol 350. The counter electrode reaction is the electrolytic reduction of erythrose:

$$\text{erythrose} + 2e^- + 2H_2O \rightarrow \text{erythritol} + 2OH^-$$

When the electrolytic oxidative decarboxylation reaction of arabinonic acid or ribonic acid to form erythrose is run as part of the same circuit as the electrolytic reduction of erythrose to erythritol, the two steps are said to run concurrently. This results in a highly efficient method for the producing of erythritol, with erythrose being produced at the anode and erythritol produced at the cathode.

The electrochemical apparatus can be configured to permit ions 400 such as cations (for example, protons) generated by the oxidative decarboxylation to be transported to the vicinity of the cathode 508. The electrochemical apparatus can comprise a means for transporting ions 506 such as cations (such as protons) between a first solution or solution portion contacting the anode into a second solution or solution portion contacting the cathode. The first solution and second solution are optionally sequestered in separate cells that can be separated by the means for transporting ions.

The electrolytic cell can have any suitable configuration. An apparatus for the decarboxylation of a reactant substrate preferably comprises an electrochemical cell. The electrochemical cell can be configured to maintain the acid solution comprising the reactants in contact with an anode (undivided configuration). Optionally, a cathode can be maintained in contact with the acid solution in the same cell as the anode, or in a separate, second half-cell (a divided configuration). In the divided configuration, a means for ion transport preferably connects the first and second cell, such as a semi-permeable membrane. Preferably, the membrane is permeable to protons or other cations. Other suitable configurations for the electrolytic cell include a flow-through reactor configuration, a packed bed configuration, a batch cell configuration, a tank cell, or a fluidized bed configuration. The electrochemical cell can be configured electrically in either a monopolar or bipolar configuration. In the monopolar configuration an electrical contact is made to each electrode. In the bipolar configuration each electrode has a cathode and an anode side and electrical connection is made only to the electrodes positioned at the ends of the cell stack comprising multiple electrodes.

U.S. Pat. No. 4,950,366, which is incorporated by reference in its entirety, discloses one example of a suitable apparatus for the decarboxylation of D-gluconic acid to yield D-arabinose that can be used to perform the oxidative decarboxylation reaction. The electrochemical cell preferably comprises an electrochemical cell anode, where the oxidative decarboxylation reaction is believed to occur.

The methods for producing erythrose using an electrolytic apparatus can yield about 20, 30, 40, 50, 60, 70, 80, 85, 90, 95 or up to 100% of the theoretical yield, preferably at least about 35%, more preferably at least about 60%, even more preferably at least about 80%, or most preferably at least about 95% or more of theoretical yield.

The methods for producing erythritol using an electrolytic apparatus can yield about 20, 30, 40, 50, 60, 70, 80, 85, 90, 95 or up to 100% of the theoretical yield, preferably at least about 35%, more preferably at least about 60%, even more preferably at least about 80%, or most preferably at least about 95% or more of theoretical yield.

Hexose Starting Materials

Figure 1B:
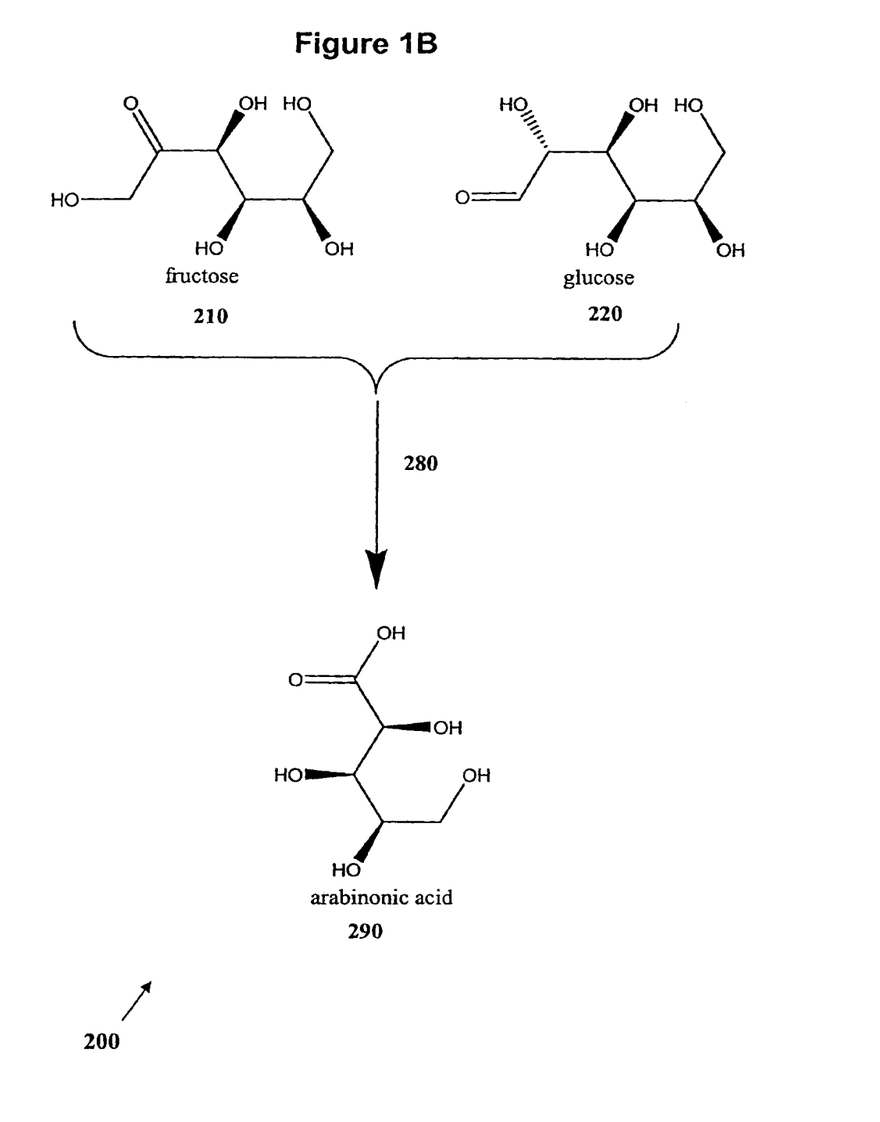
FIG. 1B is a reaction scheme using certain glucose or fructose starting materials.

In a second embodiment, the arabinonic or ribonic acid reactant can be obtained from a suitable hexose starting material by any suitable method. Referring again to FIG. 1A, preferred starting materials are selected from the group consisting of: allose 10, altrose 20, glucose 60 and mannose 70. While the D-stereoisomer of the starting materials are shown in the embodiments illustrated in FIG. 1, any suitable stereoisomer may be used, including the D-, L- or meso-forms of the illustrated starting materials. Alternatively, D-ribonic acid can be used as a starting material 40 to produce D-arabinonic acid reactant 90 by process 150, or vice versa (by process 140). Preferably, the starting material is a meso-, d- or l-form of glucose, fructose or mannose, although any suitable derivative or analog of the allose 10, altrose 20, glucose 60 or mannose 70 materials can be used as a starting material that permits conversion of the starting material to a desired reactant can be used. Fructose is also a preferred starting material. Referring to FIG. 1B, another preferred reaction scheme 200 shows the conversion of a starting material comprising fructose 210, glucose 220, or a mixture of fructose 210 and glucose 220, to arabinonic acid 290 by an oxidative decarboxylation reaction 280. The arabinonic acid 290 is preferably D-arabinonic acid 90, suitable as a reactant in the electrolytic decarboxylation reaction 100 described above with respect to FIG. 1A.

The oxidative decarboxylation reactions 30, 80, 280 can be performed on a reactant substrate using various chemical reactions. Examples of suitable chemical oxidative decarboxylation approaches include, but not limited to, the use of a transition metal ion catalyst with a primary oxidizing agent or the use of a hypochlorite/hypochlorous acid. In another aspect, a chemical oxidative decarboxylation is performed using transition metal ion catalyst such as: Fe(III) or Cu(II) with a primary oxidizing agent such as hydrogen peroxide to regenerate the catalyst. The chemical oxidative decarboxylation can be performed using a copper transition metal ion catalyst, such as a Cu(II) catalyst, in combination with any suitable primary oxidizing agent. For example, a Ruff degradation procedure can be performed, preferably using copper ions rather than iron for the Ruff degradation of acidic sugars (CS Patent 232647 and FR Patent 2771413). The Ruff degradation is described in W. Pigman et al., "The Carbohydrates," Academic Press, New York, 2nd Ed., Vol. IA (1972), Vol. IB (1980), portions of which relevant to oxidative decarboxylations of carbohydrates are incorporated herein by reference.

Referring again to FIG. 1B, the D-arabinonic acid 290 is preferably prepared by oxidizing a starting material comprising glucose 220 or fructose 210 with oxygen gas in an alkaline water solution (for example, as described in U.S. Pat. No. 4,125,559 and U.S. Pat. No. 5,831,078, incorporated herein by reference). Preferably, the starting material comprising glucose 220, fructose 210, or a mixture thereof, is reacted with an alkali metal compound in aqueous solution by first heating the alkali metal compound in aqueous solution at a temperature between about 30° C. and 100° C., then passing oxygen into the solution at a pressure of between about 1.5 to about 40 bar, and finally adding the starting material and permitting the reaction to continue for at least about 4.5 hours per mole of starting material while stirring the reaction mixture. Alternatively, the starting material can be heated initially in the aqueous solution instead of the alkali metal compound, and the alkali metal compound can be added to the reaction mixture in the last step, instead of the starting material and after the oxygen is added. The starting material is preferably a D-Hexose such as D-glucose, D-fructose or D-mannose, which can be present in various ring forms (pyranoses and furanoses) and as various diastereomers, such as α-D-glucopyranose and β-D-glucopyranose. The starting material can be reacted with the alkali metal compound in a stoichiometric amount, or in excess, preferably using an amount of from 2 to 5 equivalents of the alkali metal compound per mole of the D-hexose starting material. Preferred alkali metal compounds are hydroxides, oxides and alcholates, especially sodium or potassium compounds. Examples of suitable alkali metal compounds include potassium hydroxide, sodium hydroxide, sodium ethylene glycolate, sodium methylate, sodium propylate, sodium ethylate, sodium tripropylene glycolate and potassium tert-butylate. The oxygen is preferably used as a mixture with inert gas, such as in the form of air, with $O_2$ in a stoichoimetric amount or in excess, but preferably with an amount of from 1 to 20 moles of $O_2$ per mole of the D-hexose starting material. The reaction is preferably carried out at above 30° C., but preferably between about 40 to 60° C., and under a pressure of about 1.5 to 40 bars, preferably between 18 to 25 bars. The reaction may be performed continuously or batchwise, in a suitable solvent. The solvent is preferably water, desirably in an amount that is about 2 to 100 times, preferably from about 2 to 30 times, the weight of D-hexose starting material added. The water may be added separately, or preferably together with, the alkali metal compound or the hexose starting material, most preferably in the form of an aqueous solution of the alkali metal compound or aqueous solution of the hexose starting material. Preferably, aqueous solutions with the alkali metal compound contain about 1 to 50 weight percent of the alkali metal compound or the hexose starting material. The total reaction time is preferably between about 4.5 and 9.0 hours per mole of the hexose starting material. The reaction mixture is preferably thoroughly stirred during the entire reaction, for example by stirring at speeds of about 1,200 to about 2,000 rpm. Mixing of the reaction mixture is preferably begun after addition of the hexose starting material. Alternatively, fructose 210 (preferably, D-fructose) can be converted to D-arabinonic acid by reaction with oxygen gas in an alkaline water solution as described in J. Dubourg and P. Naffa, "Oxydation des hexoses reducteur par l'oxygene en milieu alcalin," *Memoires Presentes a la Societe Chimique*, p. 1353, incorporated herein by reference.

Figure 2:
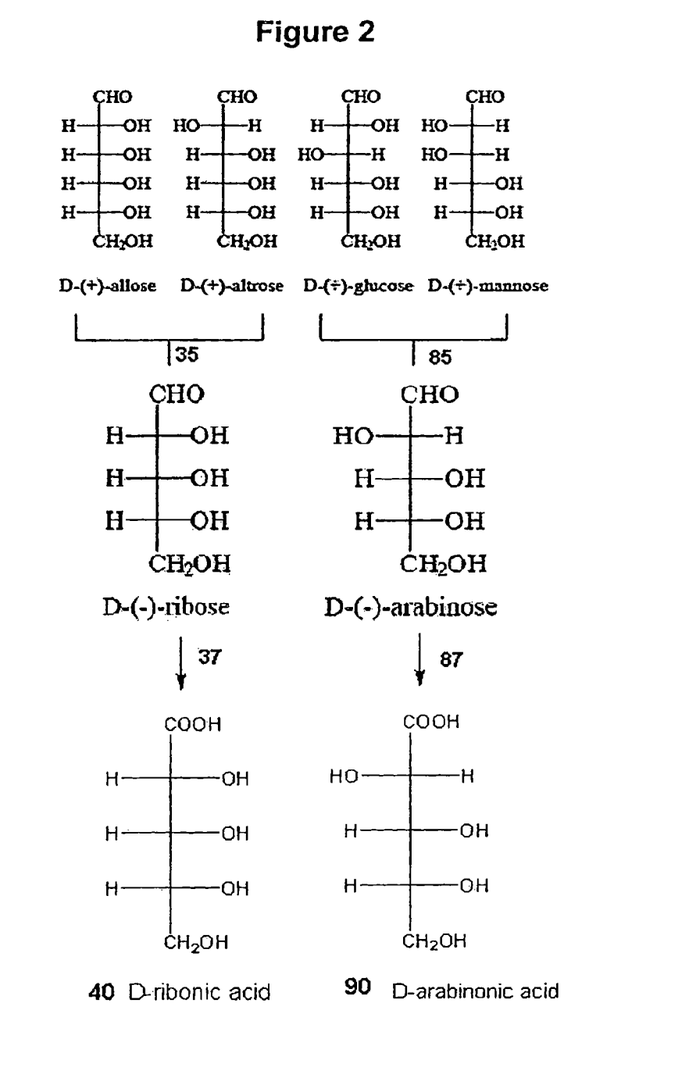
FIG. 2 is a reaction scheme showing examples of certain preferred reaction steps.

In another aspect of the second embodiment, D-arabinonic acid reactant 90 may be prepared by decarboxylation 80 of a D-glucose starting material 60 by one or more reactions. Referring to FIG. 2, the starting material can be converted to an arabinonic reactant 90 or a ribonic acid reactant 40 by one or more reaction steps. Preferably, a suitable C-6 sugar starting material is decarboxylated at the C-1 position. Optionally, a starting material comprising D-(+)-allose or D-(+)-altrose can undergo a decarboxylation reaction 35 to produce an intermediate comprising D-(−)-ribose (aldehyde) that can subsequently undergo an oxidation reaction 37 to produce the desired reactant 40 comprising D-ribonic acid. Similarly, a starting material comprising D-(+)-glucose or D-(+)-mannose can undergo a decarboxylation reaction 85 to produce an intermediate comprising D-(−)-arabinose (aldehyde) that can subsequently undergo an oxidation reaction 87 to produce the desired reactant 90 comprising D-arabinonic acid. U.S. Pat. No. 4,515,667 describes a process for the photochemical decarboxylation of an alpha-hydroxy carboxylic acid to the corresponding alcohol which process comprises irradiating a mixture of a solution of an alpha-hydroxy carboxylic acid and a metal titanate.

D-arabinonic acid can also be produced from D-glucose by oxidation of D-glucose with pyranose-2-oxidase to D-arabino-hexos-2-ulose (U.S. Pat. No. 4,423,149) and treating this with hydrogen peroxide (Carbohydr. Res. 127 (1984) 319) or other hydroperoxides. The reaction of D-arabino-hexos-2-ulose and hydrogen peroxide is fastest and most selective in alkaline solutions while the products comprise the salts of D-arabinonic and formic acids. Under acidic conditions e.g. performic acid (i.e. a mixture of formic acid and hydrogen peroxide) may be applied as the oxidant. 0.3M D-erythro-pentos-2-ulose can be oxidized with 0.6M performic acid. The reaction is complete in 10 minutes and results in the formation of D-erythrono-1,4-lactone, 3- and 4-o-formyl-D-erythronic acids and the unsubstituted D-erythronic acid. The o-formyl groups are rapidly hydrolyzed in an aqueous solution. Still another way of producing D-arabinonic acid is to oxidize D-glucose to D-arabino-2-hexylosonic acid (or its salt) and decarboxylate it with hydrogen peroxide or its salt (JP 15,610 ('63), Carbohydr. Res. 36 (1974) 283-291). D-arabino-2-Hexylosonic acid can be produced through fermentation (U.S. Pat. Nos. 3,255,093 and 3,282,795), catalytic oxidation (EP-A-O-, 151,498) or a two-step enzymatic oxidation (U.S. Pat. No. 4,423,149). The advantage of the route via D-arabino-2-hexylosonic acid is that formic acid is not generated, which enables a more direct hydrogenation of the de-ionized oxidation product mixture with the ruthenium catalyst.

Analogous or similar reactions can be performed on other starting materials to generate suitable reactant materials. In a second aspect of the second embodiment, D-arabinonic acid reactant 90 may be prepared by decarboxylation 80 of a D-mannose starting material 70 by one or more reactions. In a third aspect of the second embodiment, D-ribonic acid reactant 40 may be prepared by decarboxylation 30 of a D-allose starting material 10 by one or more reactions. In a fourth aspect of the second embodiment, D-ribonic acid reactant 40 may be prepared by decarboxylation 30 of a D-altrose starting material 20 by one or more reactions. Still other starting materials can also be used. For example, D-arabinonic acid is also formed as the main product in a similar oxidation of D-fructose (Carbohydr. Res. 141 (1985) 319).

The starting materials can also be converted to aldonic acids and subsequently reacted to form a suitable reactant such as the arabinonic acid or ribonic acid. One suitable chemical oxidative decarboxylation is performed using hypochlorite/hypochlorous acid. Amides of sugar acids can also be decarboxylated from hypochloride (Hoffman degradation). The Hoffman degradation can also be used for the decarboxylation of aldonic acid starting materials. Further details on the oxidative decarboxylation of carbohydrates using hypochlorite/hypochlorous acid are found in R. L. Whistler et al, "Preparation of D-arabinose and D-glucose with hypochlorite," Journal of the American Chemical Society, 81, 46397 (1981), which is incorporated herein by reference. Suitable starting materials such as a hexose starting material can be synthesized or obtained from any suitable source or by any suitable synthesis or purification method(s).

Conversion of Erythrose to Erythritol

In a third embodiment, an erythrose product of the electrolytic decarboxylation step can be converted to erythritol by any suitable method, during or after the oxidative decarboxylation. The conversion of erythrose to erythritol can be performed using any suitable reduction or hydrogenation reaction.

A reduction can be a hydrogenation reaction performed with hydrogen and a ruthenium (See WO Patent Appl. No. 2004/052813, incorporated herein by reference), nickel (U.S. Pat. No. 4,008,285, incorporated herein by reference), or other hydrogenation catalysts according to known art to produce polyols from aldoses. Alternatively, electrochemical reduction may be used (Taylor, *Chemical and Metallurgical Engineering*, Vol. 44 (1937) 588, which is incorporated herein by reference). Still other methods useful for the electrolytic hydrogenation of erythrose to erythritol are described in the following references: V. Anantharaman et al., "The Electrocatalytic Hydrogenation of Glucose II. Raney Nickel Powder Flow-Through Reactor Model," *J. Electrochem. Soc.*, vol. 141, No. 10, October 1994, pp. 2742-2752; and Coche et al., "Electrocatalytic Hydrogenation Using Precious Metal Microparticles in Redox-Active Polymer Films", J. Org. Chem., vol. 55, No. 23, pp. 5905-5910 (1990).

Erythrose can be reduced by using hydrogen and a hydrogenation catalyst to produce erythritol. The reduction can be performed using any suitable reaction, such as a ruthenium or nickel catalyst. In one aspect, a hydrogenation can be performed at temperatures between 70° C. and 150° C. and at pressures between 0.1 and 10 MPa $H_2$. For example, U.S. Pat. No. 6,300,049 describes certain methods for the manufacture of erythritol by hydrogenation of D-erythrose wherein from 1 to 10% by weight of catalyst is used with respect to the sugar, as dry matter, and subjected to the hydrogenation. In this reaction, the hydrogenation is preferably carried out on syrups with a dry matter content of between 15 and 50%, preferably 30 to 45%, under a hydrogen pressure of between 20 and 200 bars. Hydrogenation can be carried out continuously or batchwise. When batchwise hydrogenation is carried out, the hydrogen pressure used is generally between 30 and 60 bars and the temperature at which the hydrogenation is carried out is between 100 and 150° C. The pH of the hydrogenation mixture can be maintained by the addition of sodium hydroxide or of sodium carbonate, for example, preferably without exceeding a pH of 9.0. Preferably, the hydrogenation minimizes the production of cracking or isomerization products. Hydrogenation reaction is preferably halted when the content of reducing sugars in the reaction mixture has become less than 1%, more preferably less than 0.5% and more particularly less than 0.1%. After cooling the reaction mixture, the catalyst is removed by filtration and the D-erythritol thus obtained is demineralized through cationic and anionic resins. At this stage, the syrup preferably contains at least 90% of D-erythritol, which is readily purified by crystallization after concentrating and cooling the solutions. One example of a suitable ruthenium catalyst (20% catalyst on total dry substance) is supported on active carbon (5% Ru on carbon).

Alternatively, a hydride reducing agent may also be used to convert erythrose to erythritol. For example, erythrose produced from the electrolytic decarboxylation reaction can be converted to erythritol by adding an excess of sodium borohydrate to a solution comprising the erythrose. Examples of hydride reducing agents are sodium borohydride, lithium borohydride, lithium aluminum hydride, with potassium borohydride ($KBH_4$) or sodium borohydride being the preferred reducing agent ($NaBH_4$).

Alternatively, erythrose is converted to erythritol by electrochemical hydrogenation of erythrose. For example, the erythrose can be reduced at an electrode, preferably a cathode, formed from a support material adhered to a suitable conductive material. The electrode may have any suitable configuration, including perforated materials such as nets, metal meshes, lamellae, shaped webs, grids and smooth metal sheets. In one aspect, the cathode can be a plane-parallel electrode configured as a planar sheet, or a candle-type electrodes configured as a cylinder. In one embodiment, the electrode is preferably a cathode comprising a conducting material adhered to a porous support. The electrode can have any suitable shape and configuration including a planar sheet or tube configured as a plurality of particles impregnated in a mesh support or an aggregated layer of particles adhered to the surface of a cylindrical planar support sheet.

U.S. Pat. No. 5,919,349, filed May 20, 1997 by Huber et al., which is incorporated herein by reference, describes one suitable electrode structure comprising a layer of conductive particles adhered to a porous support. The support is preferably configured as a porous conductive material such as steel, nickel, nickel alloys, tantalum, platinized tantalum, titanium, platinized titanium, graphite, electrode carbon and similar materials, alloys and mixtures thereof. An electrically conductive material may be attached to the support material, preferably in a particulate form. The conductive material preferably forms a cathodically polarized layer when deposited on the support material. Preferably, the conductive material is formed from metal particles, conductive metal oxides or a carbonaceous material. Suitable metals for the conductive layer include Group I, II and VIII metals from the Periodic Table, especially Co, Ni, Fe, Ru, Rh, Re, Pd, Pt, Os, Ir, Ag, Cu, Zn, Pb and Cd, of which Ni, Co, Ag and Fe are preferably used as Raney Ni, Raney Co, Raney Ag and Raney Fe. The conductive material may be doped with small amounts of metals such as Mo, Cr, Au, Mn, Hg, Sn or other elements of the Periodic Table of the Elements, especially S, Se, Te, Ge, Ga, P, Pb, As, Bi and Sb. The conductive material may also be a metal oxide such as magnetite or a carbonaceous material such as graphite, activated carbon or carbon black. Particularly preferred conductive materials are particles of: Pd/C, Pt/C, Ag/C, Ru/C, Re/C, Rh/C, Ir/C, Os/C and Cu/C, optionally doped with metals or other elements of the Periodic Table of the Elements, including S, Se, Te, Ge, Ga, P, Pb, As, Bi and Sb. The conductive metal materials may be adhered to the support by any suitable method, such as reducing salts of metals in contact with the support, such as metal halides, metal phosphates, metal sulfates, metal chlorides, metal carbonates, metal nitrates and the metal salts of organic acids, preferably formates, acetates, propionates and benzoates, especially preferably acetates. The pore size of the support is generally about 1 to 500 µm, preferably about 5 to 300 µm and most preferably about 50 to 200 µm, and the porous support material preferably has a void-to-volume ratio of at least about 0.2, and preferably up to about 0.7 (i.e., up to 70% porous). The pore size of the support generally exceeds the mean diameter of the particles forming a layer of conductive material deposited on the support. Preferably the pore size of the support is about twice to four times as large as the mean particle size of the particles forming the layer. Alternatively, supports may have other pore sizes which are smaller than the mean particle size of the particles forming the layer.

In one highly preferred embodiment, the electrochemical hydrogenation of erythrose to form erythritol is done as part of the same circuit with the electrolytic decarboxylation step to form erythrose. In this way the anode is in electrically conducting communication with the cathode. The anode and cathode are connected through a means for electrical conduction. The reduction and oxidative decarboxylation steps are said to run concurrently.

The electrochemical cell cathode can be formed from any suitable material including, for example, Pb, Cu, Cd, Hg, Zn, Ni, Ru, Rh, Pt, Fe, steels, amalgams thereof or alloys thereof. Preferably, the cathode comprises Pb, Cu, Zn, Ni, or Pt. In other aspects the cathode comprises Nickel foam, Raney Nickel, or Nickel Aluminum alloy, more preferably the cathode comprises Raney Nickel. The cathode may be formed from a support material adhered to a suitable conductive material, including, for example a catalytic amount of Ru on a conducting substrate.

The electrochemical cell anode can be formed from any suitable material including, for example, graphite, pyrolytic carbon, wax-impregnated graphite, glassy carbon, dispersed graphite, dispersed carbonaceous material, carbon cloth, coke, or platinum as a planer, packed bed, fluidized bed, or porous anode. Most preferably, the anode reactant surface comprises a highly crystalline graphitic material, such as a graphite foil.

An apparatus for the decarboxylation of a reactant substrate and reduction of erythrose comprises an electrochemical cell. The electrolytic cell can have any suitable configuration. The cathode can be maintained in the same cell as the anode (undivided configuration), or in a separate, second half-cell (a divided configuration). Other suitable configurations for the electrolytic cell include a flow-through reactor configuration and a batch cell configuration.

Preferably, at least about 10% of the arabinonic or ribonic acid is neutralized or exists as a corresponding salt thereof. For example, the acid reactant solution can be provided with about 10, 20, 30, 40, 50, 60, 70, 80, 90, or 100% of one or more reactant acids neutralized. Preferably, 10%-100% of at least one ribonic acid or arabinonic acid reactant is neutralized. More preferably, about 35%-80% of a ribonic acid or arabinonic acid reactant present is neutralized, even more preferably about 40%-60%. Most preferably, about 50% of the ribonic acid or arabinonic acid reactant present in a reactant acid solution is neutralized.

The methods for producing erythrose using an electrolytic apparatus can yield about 20, 30, 40, 50, 60, 70, 80, 85, 90, 95 or up to 100% of the theoretical yield, preferably at least about 35%, more preferably at least about 60%, even more preferably at least about 80%, or most preferably at least about 95% or more of theoretical yield.

The methods for producing erythritol using an electrolytic apparatus can yield about 20, 30, 40, 50, 60, 70, 80, 85, 90, 95 or up to 100% of the theoretical yield, preferably at least about 35%, more preferably at least about 60%, even more preferably at least about 80%, or most preferably at least about 95% or more of theoretical yield.

EXAMPLES

The following examples are to be considered illustrative of various aspects of the invention and should not be construed to limit the scope of the invention, which are defined by the appended claims.

Experimental Procedure

The experiments detailed in Examples 1-2 were performed in a glass cell using a graphite foil flag anode. The glass cell consisted of a large test tube, a 5 cm² stainless steel cathode flag welded to a titanium rod, and a 5 cm² Grafoil flag (AET GrafTech, 0.03" thick) attached to a graphite rod current collector.

Example 1

Electrolytic Decarboxylation of Ribonic Acid

Sodium ribonate (15 mmoles) was dissolved in 20 mL of water. Cation exchange resin (Amberlite IRC747 H+ form) was added to lower the pH from 6.8 to 3.5 (or approximately 50% neutralization of the starting material). The solution was filtered to remove the cation resin, the ribonate starting material was diluted to 30 mL, and 25 mL transferred to glass cell for electrolysis. The initial ribonate solution was analyzed by HPLC against a standard and quantified to be 9.54 mmoles (0.38M). The 25 mL of starting material containing 9.54 mmoles of ribonate was stirred in the glass cell, while a constant current of 0.5 amps (100 mA/cm²) was applied. The cell voltage averaged about 6.5 volts, and the pH of the substrate increased from 3.5 to 7.6 after 2F/mole of charge was passed. Samples were taken at 603, 1206 and 1809 coulombs. The samples containing the erythrose product were reduced to erythritol with an excess amount of sodium borohydride, and analyzed for erythritol by HPLC-RI. The samples were quantified for erythritol based on a response factor determined from an erythritol standard, see Table 1.

TABLE 1

| Sample # | Charge F/mole | Erythritol Conc. mg/mL | Erythritol Yield, % |
|---|---|---|---|
| 652-25A | 0 | 0 | — |
| 652-25B | 0.7 | 12.8 | 27.4 |
| 652-25C | 1.3 | 28.7 | 61.7 |
| 652-25D | 2.0 | 37.8 | 81.1 |

Example 2

Electrolytic Decarboxylation of Arabinonic Acid

Potassium arabinonate (15 mmoles) was dissolved in 20 mL of water. The arabinonate was acidified to approximately 50% neutralization by adding cation exchange resin (Amberlite IRC747 H+ form) and lowering the pH from 8.4 to 3.5. The arabinonate was filtered to remove the resin, diluted to 30 mL, and transferred to a glass cell for electrolysis. The initial arabinonate was quantified by HPLC-RI against an arabinonate standard and was found to contain 9.2 mmoles (0.37 M). There was a loss of 3.3 mmoles of arabinonate from the cation exchange resin.

The 25 mL of starting material containing 9.2 mmoles of arabinonate was stirred in the glass cell, while a constant current of 0.5 amps (100 mA/cm²) was applied. The cell voltage averaged about 5.5 volts, and the pH of the substrate increased from 3.5 to 7.7 after 2F of charge was passed per mole of starting material. Samples were taken at 603, 1206 and 1809 coulombs. The samples containing erythrose were reduced to erythritol with an excess amount of sodium borohydride, and analyzed for erythritol by HPLC-RI. The samples were quantified for erythritol based on a response factor determined from a known standard, see Table 2.

TABLE 2

| Sample # | Charge F/mole | Erythritol Conc. mg/mL | Erythritol Yield, % |
|---|---|---|---|
| 652-29A | 0 | 0 | — |
| 652-29B | 0.68 | 8.1 | 12.9 |
| 652-29C | 1.4 | 24.1 | 53.3 |
| 652-29D | 2.0 | 27.3 | 60.4 |

Example 3

Electrochemical Decarboxylation of Arabinonic Acid and Erythritol Production in Single Cell An undivided electrochemical cell was constructed comprising a graphite foil anode (5 cm²) and a cathode (5 cm²) selected from Ni, Ni foam, Raney Ni, low over potential catalyzed Ni, graphite, Zn, Pb, Cu and Pt. The electrodes were approximately 3 mm apart. The cell was filled with 25 mL of electrolyte containing 0.25M arabinonic acid and 0.25M sodium arabinonate in water. The cell was run at a current density of 100 mA/cm², ambient temperature, and was stirred using a magnetic stir bar.

As the electrolysis proceeded, seven aliquots of arabinonic acid (2.13M) were added in at 300 coulomb intervals to replace the arabinonic acid consumed at the anode. The total arabinonic acid/arabinonate used in the experiments was 22 mmoles. After the last addition the electrolysis was continued until 100% theory charge had been passed based on the total arabinonate/arabinonic acid present.

The electrolyte was sampled and analyzed for arabinonic acid by ion chromatography using a conductivity detector, and erythrose and erythritol by HPLC using a refractive index detector.

The erythritol formed based on the cathode type is shown in Table 3.

TABLE 3

| Cathode | Erythritol formed (mmoles) |
|---|---|
| Ni Foam | 4.52 |
| Lead | 3.46 |
| Graphite foil | 1.36 |
| Zinc | 5.02 |
| Low overpotential Coated Ni | 5.87 |
| Pt | 4.52 |
| Cu | 5.78 |
| Raney Ni | 12.33 |
| Graphite | 0.23 |

Theoretical Example 1

Oxidative Decarboxylation of Glucose Starting Material to Form Arabinonate

One suitable example of a reaction for the oxidative decarboxylation of a glucose starting material to arabinonate is provided in U.S. Pat. No. 4,125,559 to Scholz et al., filed May 19, 1977 and issued Nov. 14, 1978, which is provided as Theoretical Example 1. A solution of 396.07 grams of KOH in 10,000 grams of water is introduced into a vertical tubular reactor of 2,000 mm length and 50 mm internal diameter which is packed with V2A steel Raschig rings of 6 mm diameter. The solution is heated to 45° C. and is mixed by means of a centrifugal pump, with a mixing effect corresponding to 1,950 revolutions per minute. 120 grams of oxygen are introduced from the reactor top and the pressure is set to 20.5 bars. In the course of 5 minutes 1,000 grams of an aqueous solution containing 396.32 grams of D-glucose, monohydrate are added, using a metering pump, at the reactor top, to the alkaline solution, which is circulated by means of the centrifugal pump (1,950 revolutions per minute) in a downward direction via the reactor top. The solution is now mixed for 9 hours at 1,950 revolutions per minute and kept at 45° C. and 20.5 bars. It is then concentrated under 15 mbars until 500 grams of residue are left. This material is introduced into 6,000 grams of methanol, while stirring, whereupon crystalline potassium arabinonate precipitates. Filtration gives a theoretical yield of 408.44 grams of potassium arabinonate of melting point 203-204° C. (with decomposition).

TABLE 4

| $^{13}$C-NMR spectrum data [internal standard: sodium salt of 3-(trimethylsilyl)-propanesulphonicacid] | |
| --- | --- |
| Carbon atom | $^{13}$C-NMR chemical shift (ppm) |
| 1 | 181.9 |
| 2 | 75.0 |
| 3 | 74.4 |
| 4 | 74.1 |
| 5 | 65/0 |

Theoretical Examples 2-5

Oxidative Decarboxylation and Hydrogenation of Glucose to Arabinitol

Other suitable examples of reactions for the oxidative decarboxylation of a glucose starting material to arabinonate, and the conversion of arabinonate to arabinitol, are provided in U.S. Pat. No. 5,831,078 to Elseviers et al., filed Jul. 23, 1997 and issued Nov. 3, 1998, which are provided as Theoretical Examples 2-5 below.

Theoretical Example 2

Oxidative Decarboxylation Applying Oxygen Gas at 2 Bar Pressure

A glucose solution (1.5 kg—10% w/w solution) starting material is heated to 45° C. in a two liter autoclave while stirring at 1000 rpm. The reactor containing the glucose solution is purged twice for 0.5 minutes with oxygen gas at 1 bar pressure. After purging, the oxygen pressure in the reactor is adjusted to 2 bar. The reaction is started by dosing the potassium hydroxide solution (242 g—50% w/w solution) with a dosing burette to the glucose solution using a dosing speed of 1.3 mol KOH/h. The total dosing time required is 1.7 hours. The reaction mixture is stirred for a total reaction time of 5 hours, including the dosing time of the alkali. The product is determined by HPLC analysis (see Table 5).

TABLE 5

| Theoretical Example No. | $H_2O_2$ used? | $O_2$ atmospheric pressure | $O_2$ at 2 bar pressure |
| --- | --- | --- | --- |
| 2 | No | 55% | 88% |
| 3 | Yes | N/A | 83% |

Theoretical Example 3

Oxidative Decarboxylation with Oxygen Pressure of 2 Bar and Addition of Hydrogen Peroxide The experiment of theoretical example 2 may be performed using glucose solutions at 10%, 20% and 30% dry substance, applying 2 bar oxygen pressure at 40°

The glucose solution is heated to 40° C. in a two liter autoclave while stirring at 1000 ppm. The reactor containing the glucose solution is purged twice for 0.5 minutes with oxygen gas at 1 bar pressure. After purging, the oxygen pressure in the reactor is adjusted to 2 bar. The reaction is started by dosing the sodium hydroxide solution (45% w/w solution) with a dosing burette to the glucose solution using a dosing speed of 0.65 mol NaOH/h.

TABLE 6

| Glucose starting material conc'n | Molar yield arabinonate |
| --- | --- |
| 10% | 89% |
| 20% | 87% |
| 30% | 80% |

Theoretical Example 4

Purification of Arabinonate, Followed by Protonation and Hydrogenation to Arabinitol Crystallization Before crystallizing the alkali metal arabinonate (being sodium arabinonate or potassium arabinonate), the crude reaction mixture is brought to pH=7 with the aid of ion exchange resin (e.g. Lewatit S2528).

The resulting reacting mixture (pH=7) is concentrated under reduced pressure at 50° C. to 70% dry substance. The crystals are collected by filtration or centrifugation and are dried at room temperature. Sodium arabinonate is obtained in 95-97% purity and potassium arabinonate is obtained in 98-99% purity. The remaining impurities are glycolate and formate.

Recrystallization

The collected crystals are dissolved again in water to obtain a 70% solution. Cooling down to room temperature allows the crystallization of sodium arabinonate, obtained in 100% purity. This recrystallization is most of the time required to remove all traces of formate. Complete removal is preferred because any trace of formic acid may poison the catalyst.

Theoretical Example 5

Protonation with Ion Exchange Resin

The protonation of alkali metal arabinonate to arabinonic acid is preferably performed with ion exchange resin (e.g.

Mitsubishi UBK 550, Lewatit S2528). This arabinonic acid is then used as a starting material for the electrolytic decarboxylation.

The described embodiments and examples are to be considered in all respects only as illustrative and not restrictive, and the scope of the invention is, therefore, indicated by the appended claims rather than by the foregoing description. All changes which come within the meaning and range of equivalency of the claims are to be embraced within their scope.

We claim:

1. A method of producing erythritol, comprising:
    providing a solution comprising arabinonic acid or ribonic acid at no more than 100% neutralization, wherein at least 10% of the arabinonic acid or ribonic acid is neutralized;
    electrolytically oxidatively decarboxylating the arabinonic acid or ribonic acid at an anode to produce erythrose;
    electrolytically reducing the erythrose at a cathode to produce erythritol; and
    maintaining the degree of neutralization of the arabinonic acid or ribonic acid at more than 10% and less than or equal to 100%.

2. The method of claim 1, wherein the decarboxylating and reducing are done concurrently as part of the same circuit.

3. The method of claim 2, wherein the reducing of the erythrose occurs by contacting the erythrose with the cathode which comprises Pb, Cu, Cd, Hg, Zn, Ni, Ru, Pt, Fe, Rh, steels, amalgams thereof or alloys thereof.

4. The method of claim 3, wherein the reducing of the erythrose occurs by contacting the erythrose with the cathode which comprises Pb, Cu, Zn, Ni, or Pt.

5. The method of claim 2, wherein the reducing of the erythrose occurs by contacting the erythrose with the cathode which comprises nickel foam, Raney nickel, or nickel aluminum alloy.

6. The method of claim 2, wherein the reducing of the erythrose occurs by contacting the erythrose with the cathode which comprises Raney nickel.

7. The method of claim 2, wherein the arabinonic acid or ribonic acid is added with a passing of current to maintain the solution having between about 35% and 80% of the arabinonic acid or ribonic acid neutralized.

8. The method of claim 2,
    wherein the reducing of the erythrose occurs by contacting the erythrose with the cathode which comprises a conducting substrate selected from the group consisting of Pb, Cd, Hg, Zn, Ni, Ru, Rh, Pt, Fe, steels, amalgams thereof, and alloys thereof; and
    wherein the arabinonic acid or ribonic acid is added with a passing of current to maintain the solution having between about 35% and 80% of the arabinonic acid or ribonic acid neutralized.

9. The method of claim 2,
    wherein the reducing of the erythrose occurs by contacting the erythrose with the cathode which comprising nickel foam, Raney nickel, nickel aluminum alloy, or a catalytic amount of Ru on a conducting substrate; and
    the wherein arabinonic acid or ribonic acid is added with a passing of current to maintain the solution having between about 35% and 80% of the arabinonic acid or ribonic acid neutralized.

10. The method of 9, wherein the anode is a graphite foil electrode.

11. The method of 9, wherein between about 40% and 60% of the arabinonic acid or ribonic acid is neutralized.

12. The method of claim 9, further comprising removing residual arabinonic acid or ribonic acid from an erythritol product formed via contacting the solution with an ion exchange resin or by electrodialysis.

13. The method of claim 1, wherein the reducing of the erythrose occurs by contacting the erythrose with the cathode which comprises a catalytic amount of Ru on a conducting substrate.

14. The method of claim 2, wherein the cathode comprises Raney nickel, and the anode is a graphite foil anode.

15. The method of claim 14, wherein between about 40% and 60% of the arabinonic acid or ribonic acid is neutralized.

16. The method of claim 2, wherein between about 40% and 60% of the arabinonic acid or ribonic acid is neutralized.

17. The method of claim 2, further comprising removing residual arabinonic acid or ribonic acid from an erythritol product formed via contacting the solution with an ion exchange resin.

18. The method of claim 2, further comprising removing residual arabinonic acid or ribonic acid from an erythritol product formed by electrodialysis.

* * * * *

UNITED STATES PATENT AND TRADEMARK OFFICE
CERTIFICATE OF CORRECTION

| | |
|---|---|
| PATENT NO. | : 9,133,554 B2 |
| APPLICATION NO. | : 13/152849 |
| DATED | : September 15, 2015 |
| INVENTOR(S) | : Jonathan A. Stapley et al. |

It is certified that error appears in the above-identified patent and that said Letters Patent is hereby corrected as shown below:

In the Claims

In column 22, claim 9, line 13, after "with the cathode which" replace "comprising" with --comprises--.

Signed and Sealed this
Tenth Day of May, 2016

Michelle K. Lee
*Director of the United States Patent and Trademark Office*